United States Patent
McGillicuddy

(10) Patent No.: US 10,568,661 B2
(45) Date of Patent: Feb. 25, 2020

(54) BONE MARROW ACCESS DEVICE

(71) Applicant: EndoCellutions, Inc., Marshfield, MA (US)

(72) Inventor: Andrew McGillicuddy, Hanover, MA (US)

(73) Assignee: EndoCellutions, Inc., Marshfield, MA (US)

( * ) Notice: Subject to any disclaimer, the term of this patent is extended or adjusted under 35 U.S.C. 154(b) by 19 days.

(21) Appl. No.: 15/721,123

(22) Filed: Sep. 29, 2017

(65) Prior Publication Data

US 2018/0085144 A1    Mar. 29, 2018

Related U.S. Application Data

(60) Provisional application No. 62/467,899, filed on Mar. 7, 2017, provisional application No. 62/467,473, filed
(Continued)

(51) Int. Cl.
*A61B 10/02* (2006.01)
*A61B 17/34* (2006.01)
(Continued)

(52) U.S. Cl.
CPC ........ *A61B 17/3472* (2013.01); *A61B 10/025* (2013.01); *A61B 10/0266* (2013.01);
(Continued)

(58) Field of Classification Search
None
See application file for complete search history.

(56) References Cited

U.S. PATENT DOCUMENTS

| 3,893,445 A | 7/1975 | Hofsess |
| 4,010,737 A | 3/1977 | Vilaghy et al. |
| (Continued) | | |

FOREIGN PATENT DOCUMENTS

| WO | 2006/027549 A1 | 3/2006 |
| WO | 2010/138895 A2 | 12/2010 |
| (Continued) | | |

OTHER PUBLICATIONS

U.S. Non-Final Office Action for U.S. Appl. No. 15/110,520 entitled, "Bone Marrow Harvesting Needle Improvements," dated Dec. 17, 2018.
(Continued)

*Primary Examiner* — Etsub D Berhanu
(74) *Attorney, Agent, or Firm* — Hamilton, Brook, Smith & Reynolds, P.C.

(57) ABSTRACT

A bone marrow access device includes a cannula and a sharp stylet removably positioned in the cannula. The cannula defines a distal opening at a distal tip and a side aperture in a side of the cannula, proximally from the distal opening. The stylet has a sharp distal tip and extends beyond the distal opening. A plug is receivable in the cannula distal to the side aperture to seal the distal opening when the stylet is removed. A method of accessing bone includes inserting the cannula and sharp stylet positioned in the cannula into bone; removing the sharp stylet from the cannula; pushing a plug through the cannula and distal to the side aperture to seal the distal opening of the cannula; and accessing the bone through the side aperture. Accessing the bone can include aspirating bone marrow, injecting a substance, or inserting an instrument into the bone.

22 Claims, 17 Drawing Sheets

FIG. 7B

Related U.S. Application Data on Mar. 6, 2017, provisional application No. 62/403,480, filed on Oct. 3, 2016, provisional application No. 62/401,255, filed on Sep. 29, 2016.

(51) Int. Cl.
*A61M 39/02* (2006.01)
*A61B 90/00* (2016.01)

(52) U.S. Cl.
CPC ..... *A61B 17/3423* (2013.01); *A61M 39/0247* (2013.01); *A61B 2010/0258* (2013.01); *A61B 2017/3456* (2013.01); *A61B 2090/034* (2016.02); *A61M 2039/0202* (2013.01); *A61M 2039/0205* (2013.01); *A61M 2039/025* (2013.01)

(56) References Cited

U.S. PATENT DOCUMENTS

| | | | |
|---|---|---|---|
| 4,249,541 A | 2/1981 | Pratt | |
| 4,262,676 A * | 4/1981 | Jamshidi | A61B 10/0283 600/566 |
| 4,356,828 A | 11/1982 | Jamshidi | |
| 4,366,822 A | 1/1983 | Altshuler | |
| 4,469,109 A | 9/1984 | Mehl | |
| 4,487,209 A | 12/1984 | Mehl | |
| 4,630,616 A | 12/1986 | Tretinyak | |
| 4,649,918 A | 3/1987 | Pegg et al. | |
| 4,796,363 A | 1/1989 | Rutter et al. | |
| 4,838,282 A | 6/1989 | Strasser et al. | |
| 5,026,350 A | 6/1991 | Tanaka et al. | |
| 5,027,827 A | 7/1991 | Code et al. | |
| 5,279,306 A | 1/1994 | Mehl | |
| 5,331,972 A | 7/1994 | Wadhwani et al. | |
| 5,357,974 A | 10/1994 | Baldridge | |
| 5,368,046 A | 11/1994 | Scarfone et al. | |
| 5,429,138 A | 7/1995 | Jamshidi | |
| 5,522,398 A | 6/1996 | Goldenberg et al. | |
| 5,526,821 A | 6/1996 | Jamshidi | |
| 5,807,275 A | 9/1998 | Jamshidi | |
| 5,807,276 A | 9/1998 | Russin | |
| 5,833,628 A | 11/1998 | Yuan et al. | |
| 5,954,671 A | 9/1999 | O'Neill | |
| 6,007,496 A | 12/1999 | Brannon | |
| 6,063,037 A | 5/2000 | Mittermeier et al. | |
| 6,080,115 A | 6/2000 | Rubinstein | |
| 6,090,121 A | 7/2000 | Weber et al. | |
| 6,110,128 A | 8/2000 | Andelin et al. | |
| 6,264,618 B1 | 7/2001 | Landi et al. | |
| 6,302,852 B1 | 10/2001 | Fleming et al. | |
| 6,312,394 B1 | 11/2001 | Fleming, III | |
| 6,416,484 B1 | 7/2002 | Miller et al. | |
| 6,425,887 B1 | 7/2002 | McGuckin et al. | |
| 6,478,751 B1 | 11/2002 | Krueger et al. | |
| 6,554,778 B1 | 4/2003 | Fleming | |
| 6,554,803 B1 | 4/2003 | Ashman | |
| 6,730,043 B2 | 5/2004 | Krueger et al. | |
| 6,755,793 B2 | 6/2004 | Lamoureux et al. | |
| 6,849,051 B2 | 2/2005 | Sramek et al. | |
| 6,905,489 B2 | 6/2005 | Mantell et al. | |
| 6,916,292 B2 | 7/2005 | Morawski et al. | |
| 6,981,948 B2 | 1/2006 | Pellegrino et al. | |
| 7,081,123 B2 | 7/2006 | Merboth et al. | |
| 7,179,232 B2 | 2/2007 | Sutton et al. | |
| 7,278,972 B2 | 10/2007 | Lamoureux et al. | |
| 7,462,181 B2 | 12/2008 | Kraft et al. | |
| 7,637,872 B1 | 12/2009 | Fox | |
| 7,850,651 B2 | 12/2010 | Allee et al. | |
| 8,043,253 B2 | 10/2011 | Kraft et al. | |
| 8,343,133 B2 | 1/2013 | Allee et al. | |
| 9,017,298 B2 | 4/2015 | Allee et al. | |
| 9,226,732 B2 | 1/2016 | Azimpoor | |
| 10,231,716 B2 | 3/2019 | McGillicuddy et al. | |
| 2001/0001811 A1 * | 5/2001 | Burney | A61B 10/0233 604/93.01 |
| 2003/0050574 A1 | 3/2003 | Krueger | |
| 2004/0077973 A1 | 4/2004 | Groenke et al. | |
| 2004/0127814 A1 | 7/2004 | Negroni | |
| 2004/0153005 A1 | 8/2004 | Krueger | |
| 2004/0191897 A1 | 9/2004 | Muschler | |
| 2006/0247552 A1 | 11/2006 | Ikehara et al. | |
| 2006/0276747 A1 | 12/2006 | Moos et al. | |
| 2007/0016100 A1 | 1/2007 | Miller | |
| 2007/0055282 A1 | 3/2007 | Muschler | |
| 2007/0066987 A1 * | 3/2007 | Scanlan, Jr. | A61B 10/025 606/184 |
| 2007/0198043 A1 | 8/2007 | Cox et al. | |
| 2007/0293788 A1 | 12/2007 | Entrekin et al. | |
| 2008/0045857 A1 | 2/2008 | Miller et al. | |
| 2008/0214957 A1 | 9/2008 | Verra et al. | |
| 2009/0149774 A1 | 6/2009 | Simon et al. | |
| 2010/0069843 A1 | 3/2010 | Allee et al. | |
| 2010/0280410 A1 | 11/2010 | Moos et al. | |
| 2011/0082425 A1 | 4/2011 | Wuestemann et al. | |
| 2011/0112436 A1 | 5/2011 | Jones et al. | |
| 2012/0035501 A1 | 2/2012 | Landrigan et al. | |
| 2012/0116247 A1 | 5/2012 | Wawrzyniak et al. | |
| 2012/0129676 A1 | 5/2012 | Duffy et al. | |
| 2012/0136277 A1 | 5/2012 | Landrigan et al. | |
| 2013/0131545 A1 | 5/2013 | Azimpoor | |
| 2013/0150752 A1 | 6/2013 | Swann | |
| 2014/0081318 A1 | 3/2014 | Houser et al. | |
| 2015/0289858 A1 | 10/2015 | McGillicuddy et al. | |
| 2016/0106462 A1 | 4/2016 | McGillicuddy et al. | |
| 2016/0331878 A1 | 11/2016 | McGillicuddy et al. | |
| 2019/0314004 A1 | 10/2019 | McGillicuddy et al. | |

FOREIGN PATENT DOCUMENTS

| | | |
|---|---|---|
| WO | 2012/047984 A1 | 4/2012 |
| WO | 2010/138895 A3 | 12/2012 |
| WO | 2013/096419 A1 | 6/2013 |
| WO | 2014/070804 A1 | 5/2014 |
| WO | 2015/109100 A1 | 7/2015 |

OTHER PUBLICATIONS

Notice of Allowance, "Apparatus and Methods for Aspirating Tissue," U.S. Appl. No. 14/439,022, dated Nov. 2, 2018.
Definition of offset (Dictionary.com on Jun. 4, 2018).
U.S. Final Office Action for U.S. Appl. No. 14/439,022 dated May 2, 2018, entitled "Apparatus and Methods for Aspirating Tissue," 21 pages.
U.S. Final Office Action for U.S. Appl. No. 14/885,821 dated Jun. 14, 2018, entitled "Bone Marrow Aspiration Device and Method," 21 pages.
Harrell, D.V., et al., "Novel Technology to Increase Concentrations of Stem and Progenitor Cells in Marrow Aspiration," downloaded from www.marrowcellutions.com on Oct. 7, 2015 (8 pages).
Ranfac—Endocellutions, "Legacy Needles are designed to pull a Small Aspirate From a Single Location," downloaded from www.marrowcellutions.com on Oct. 7, 2015 (1 page).
Ranfac—Endocellutions, "Marrow Cellution™—Bone Marrow Harvesting Systems," downloaded from www.marrowcellutions.com on Oct. 7, 2015 (2 pages).
Ranfac—Endocellutions, Presentation, "Marrow Cellution," downloaded from www.marrowcellutions.com on Oct. 7, 2015 (5 pages).
Ranfac, Fact Sheet, "Marrow Cellution—Bone Marrow Aspiration and Stem Cell Harvesting Systems," downloaded from www.marrowcellutions.com on Dec. 23, 2015 (2 pages).
Scarpone, M. A. et al., "Marrow Cellution Bone Marrow Aspiration System and Related Concentrations of Stem and Progenitor Cells," downloaded from www.marrowcellutions.com on Dec. 23, 2015 (6 pages).
Snarecoil™ Biopsy Needles—Technology that reduces the TIME and TRAUMA of Bone Marrow Biopsies, retrieved from www.ranfac.com/pdf/bonemarrow.pdf, Mar. 15, 2010, (4 pages).
Notification of Transmittal of the International Search Report and the Written Opinion of the International Searching Authority, or the Declaration, "Apparatus and Methods for Aspirating and Separating

(56) References Cited

OTHER PUBLICATIONS

Components of Different Densities From a Physiological Fluid Containing Cells", dated Aug. 18, 2011.
International Search Report and Written Opinion, PCT/US2013/067358, "Apparatus and Methods for Aspirating Tissue," dated Feb. 21, 2014.
International Preliminary Report on Patentability and Written Opinion, PCT/US2013/067358, "Apparatus and Methods for Aspirating Tissue," dated May 5, 2015.
International Search Report and Written Opinion, PCT/US2015/011614, "Bone Marrow Harvesting Needle Improvements," dated Apr. 20, 2015.
Notification Concerning Transmittal of International Preliminary Report on Patentability, PCT/US2015/011614, "Bone Marrow Harvesting Needle Improvements," dated Jul. 28, 2016.
U.S. Office Action for U.S. Appl. No. 14/885,821 dated Sep. 11, 2017, entitled "Bone Marrow Aspiration Device and Method," 34 pages.
U.S. Office Action for U.S. Appl. No. 14/439,022 dated Sep. 5, 2017, entitled "Apparatus and Methods for Aspirating Tissue," 27 pages.
U.S. Office Action for U.S. Appl. No. 14/885,821, dated Apr. 5, 2019 entitled "Bone Marrow Aspiration Device and Method,".
U.S. Office Action for U.S. Appl. No. 15/110,520, dated Apr. 17, 2019 entitled "Bone Marrow Harvesting Needle Improvements,".
Al-Ibraheemi et al., "Comparison between 1-needle technique versus 2-needle technique for bone marrow aspiration and biopsy procedures," Arch Pathol Lab Med., 137(7): 974-8, Jul. 2013.
Islam, A., "Bone marrow aspiration before bone marrow core biopsy using the same bone marrow biopsy needle: a good or bad practice?," J Clin Pathol., 60(2): 212-215, Feb. 2007.
Notice of Allowance and Fees Due, U.S. Appl. No. 15/110,520, entitled "Bone Marrow Harvesting Needle Improvements," dated Oct. 1, 2019.

* cited by examiner

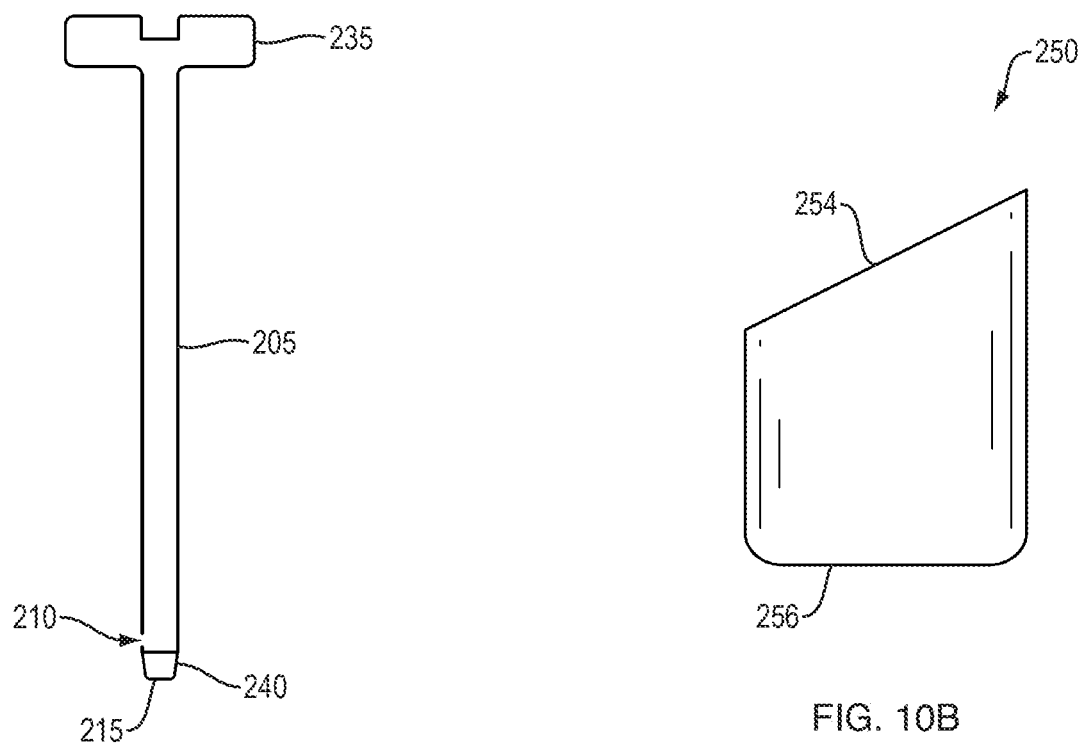
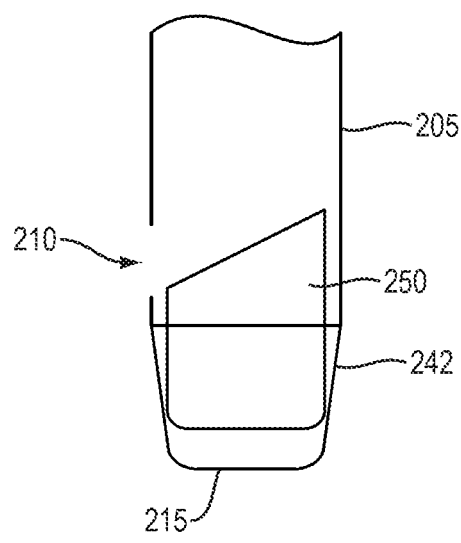
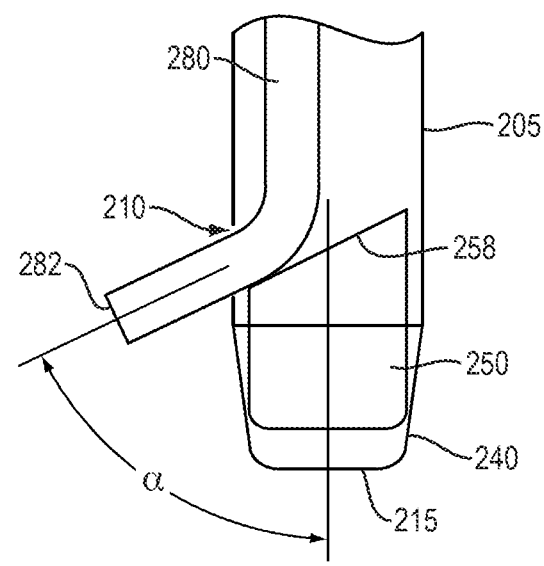
FIG. 10A
FIG. 10B
FIG. 10C
FIG. 10D

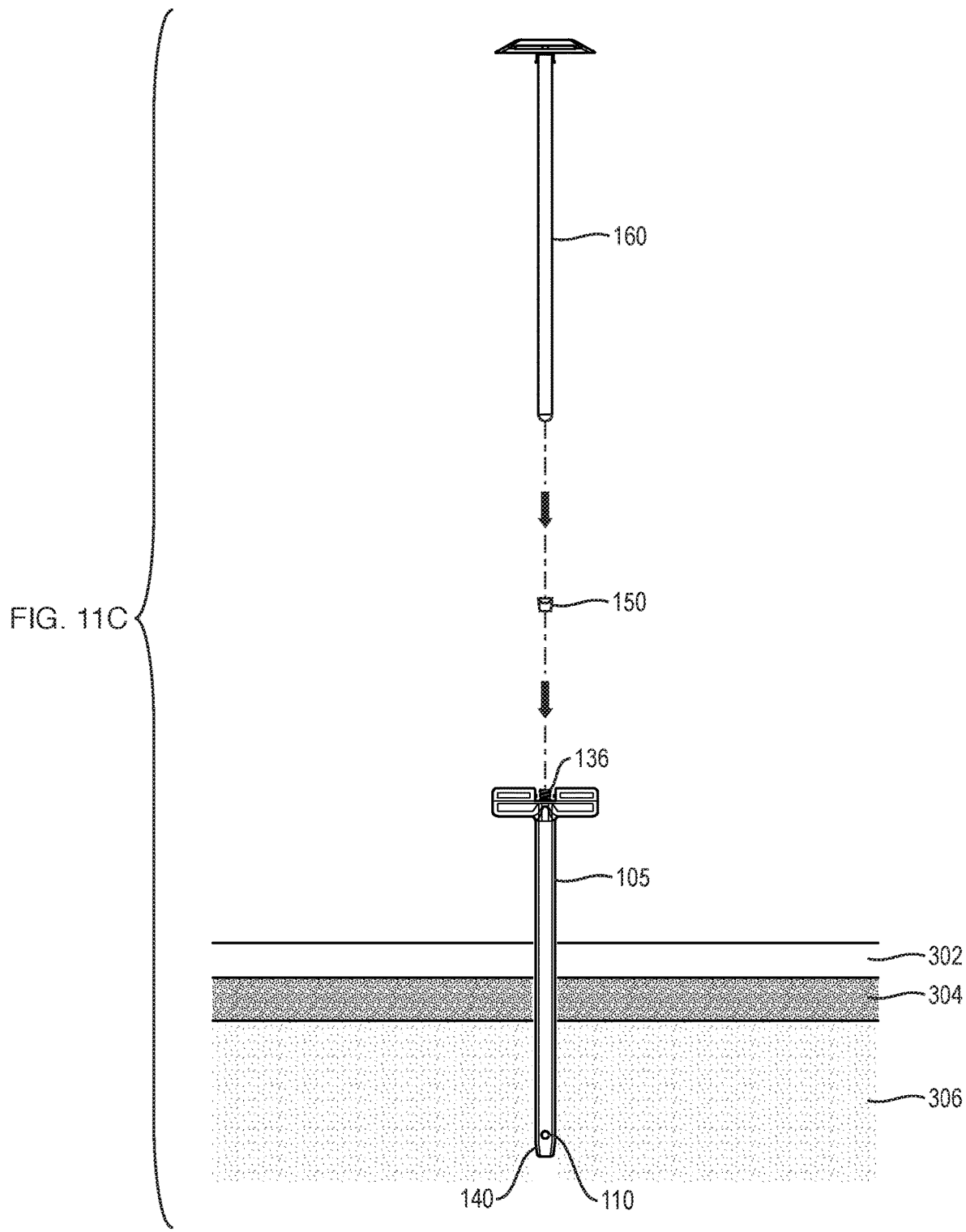

BONE MARROW ACCESS DEVICE

RELATED APPLICATIONS

This application claims the benefit of U.S. Provisional Application No. 62/467,899, filed on Mar. 7, 2017, U.S. Provisional Application No. 62/467,473, filed on Mar. 6, 2017, U.S. Provisional Application No. 62/403,480, filed on Oct. 3, 2016, and U.S. Provisional Application No. 62/401,255, filed on Sep. 29, 2016. The entire teachings of the above applications are incorporated herein by reference.

BACKGROUND

A marrow aspiration device is designed to take a liquid sample of bone marrow tissue. Typically, a device that is utilized to aspirate samples from bone consists of a hollow cannula that surrounds a stylet. The stylet includes a sharp distal tip which extends outwardly from a distal opening of the cannula when the stylet is placed inside the cannula. The combined cannula and stylet are used to penetrate through the outer layer of the bone, called the cortex, which is considerably harder than the inner layer, called trabecular bone, and the tissue within the trabecular bone that is sampled, referred to as the marrow. Once the stylet and cannula have penetrated the cortex, the stylet is removed which exposes a connector in the handle that is attached to the cannula. A syringe is attached to the connector, negative pressure is applied by pulling on the plunger handle of the syringe, and a sample of tissue from the bone space is retrieved into the syringe.

Blood and marrow have different viscosities and cellular characteristics. Blood has a lower viscosity than marrow. The goal of a good aspirate is to retrieve as much marrow and as little blood as possible. However, since blood has a lower viscosity, it preferentially flows in response to the negative pressure created by the syringe. Inserting a cannula with a sharp stylet into the bone space breaks the inner trabecular bone as a path is created equal to the outer diameter of the cannula. The sharp stylet protrudes from the end of the cannula. Removing the sharp stylet creates a void equal to the portion of the stylet that extended beyond the distal end of the cannula. Upon removal of the stylet, blood fills that void as the pressure created by the stylet, which was preventing greater bleeding, is removed. This blood is now in contact with the opening at the end of the cannula. Applying negative pressure will create the greatest pressure against the opening which is in contact with the lower viscous tissue. Therefore, a typical aspiration device will preferentially draw blood over marrow even if the cannula has small side apertures. Pulling the cannula back while aspirating creates a longer channel that fills with blood and exacerbates the problem of preferentially drawing blood. Since there are only a finite number of marrow cells in any given location of the trabecular bone space, drawing all of a sample from a single location by not moving the cannula during the aspiration process gives a rapidly diminishing return on the number of cells after only drawing a small sample (e.g., 1 mL).

Therefore, there is a need for a system that aspirates marrow in a manner that minimizes the level of peripheral blood.

SUMMARY

The present invention relates to bone marrow access devices and methods useful for aspirating bone marrow, delivering a substance into bone, or inserting an instrument into bone.

A bone marrow access device includes a cannula and a sharp stylet removably positioned in the cannula. The cannula defines a distal opening at a distal tip of the cannula and a side aperture in a side of the cannula and positioned proximally from the distal opening. The stylet has a sharp distal tip and extends beyond the distal opening. A plug is receivable in the cannula distal to the side aperture to seal the distal opening of the cannula when the sharp stylet is removed.

The device can further include a blunt stylet having a blunt distal tip, the blunt stylet receivable in the cannula when the sharp stylet is removed. The blunt stylet is receivable in the cannula before the plug is received in the cannula.

The cannula can define plural side apertures. The side apertures can be on the same side of the cannula or on opposite side of the cannula. The apertures may be positioned at different distances from the distal opening of the cannula. In an embodiment, the cannula includes one or more apertures on one side of the cannula and corresponding aperture(s) on the other side of the cannula, the corresponding aperture(s) being axially and radially aligned.

A portion or all of the cannula can be flexible. For example, the cannula can include steel, laser cut steel to add flexibility, plastic, such as PEEK, or a combination thereof.

The cannula can be tapered. For example, the cannula can include a tapered internal surface near the distal tip of the cannula. The plug can be configured to securely lodge against the tapered internal surface and distal to the side aperture(s) of the cannula.

In one example, an external surface of the plug is tapered to complement the tapered internal surface of the cannula.

An outer dimension of the plug can be less than an inner diameter of the cannula proximal to the tapered internal surface and greater than an inner diameter of the cannula at the tapered internal surface. This configuration allows the plug to be pushed distally through the cannula such that the plug lodges in the distal, tapered end of the cannula.

In one example, the plug is substantially cylindrical. In another example, the plug is substantially spherical. The plug can be easily deformable or rigid.

A distal end of the plug can be blunt, to seal the distal opening of the cannula.

A proximal end of the plug can be sloped. The side aperture in the cannula can be a slot having an elongated shape. The device can be configured to align the sloped end of the plug with the slot in the cannula when the plug is received in the cannula and sealing the distal opening. In an embodiment, the cannula defines a single side slot.

The device can include a push rod receivable in the cannula to deploy the plug into the cannula to seal the distal opening. The push rod can have a length such that at its limit the push rod is not at the distal opening. A distal end of the push rod can be configured to interface with the proximal end of the plug. The plug and the push rod may define complementary features. For example, the distal end of the push rod can be convex and the proximal end of the plug can be concave. The push rod may be partially receivable in the plug, the plug capping the distal end of the push rod.

The device can include a handle assembly including a cannula handle attached to the cannula and a stylet handle attached to the sharp stylet, the cannula and stylet handles configured to interlock to secure the stylet in the cannula.

The device can further include a connector to connect to a syringe, or other suitable device, for aspirating or delivering material through the cannula. The connector can be at the cannula handle. The stylet handle can be configured to cover the connector when the stylet and cannula handles interlock.

The device can further include an adjustable depth guide to move the cannula when the cannula is positioned within bone. The depth guide can include a lead screw attached to the cannula handle and a threaded jacket receivable on the lead screw.

A method of accessing bone includes inserting a cannula and a sharp stylet positioned in the cannula into bone. The cannula defines at least one side aperture in a side of the cannula and a distal opening at a distal tip of the cannula. The stylet has a sharp distal tip that extends through the distal opening. The method further includes removing the sharp stylet from the cannula, pushing a plug through the cannula and distal to the side aperture to seal the distal opening of the cannula, and accessing the bone through the side aperture of the cannula.

Accessing the bone can include aspirating bone marrow through the side aperture, injecting a substance into the bone through the side aperture, or inserting an instrument through the side aperture into the bone.

Pushing the plug through the cannula can include pushing the plug with a push rod receivable in the cannula.

Inserting the cannula and stylet into the bone can include advancing the cannula and stylet into the bone with an adjustable depth guide. The method can further include withdrawing the cannula from the bone with the adjustable depth guide.

The present invention provides, in one embodiment, a marrow aspiration device capable of aspirating a sample of marrow while minimizing the amount of peripheral blood obtained within the aspirated marrow. The aspiration device can include an outer cannula secured to a standard Luer fitting that can mate with a syringe. The Luer fitting can be part of a handle that is attached to the cannula. The cannula can be tapered on the end and has at least one aperture. A stylet that can have a handle that mates to the handle connected to the cannula may be provided. A delivery rod (e.g., push rod) that fits into the cannula when the stylet is removed, and a plug that fits into the cannula is provided. The cannula defines a distal tip that can be tapered. The stylet is designed to be inserted in the cannula and defines a sharp distal tip. The sharp stylet can be designed to extend beyond the distal end of the cannula. A second blunt stylet designed to be inserted in the outer cannula is optionally provided and can be of varying lengths.

The plug can be designed to be inserted through the Luer fitting and into the tapered hollow cannula. The delivery rod can be used to assist in placing the plug. The optional blunt stylet can be used as the delivery rod. In an embodiment where the distal cannula is tapered, the outer dimension of the plug is less than the inner diameter of the cannula on the proximal end (near the handle) but greater than the inner diameter of the cannula on the tapered distal end. The aperture can be on the distal end of the cannula where the inner dimension of the cannula is greater than the outer dimension of the plug; consequently, the plug will lodge (press fit) into the distal end of the cannula past the aperture in the cannula. The outer dimension of the plug is wider than the tapered inner diameter of the cannula and therefore cannot pass through the distal end of the cannula. The outer dimension of the plug is narrower than the inner diameter of the cannula on the proximal end above the taper and therefore can pass through the cannula, past the aperture until it hits the tapered distal end. The plug is designed to lodge in the cannula below the aperture in the tapered distal end. In this configuration, the end hole of the cannula is plugged by the plug and the side aperture remains open.

Various configurations of the plug, cannula, and push rod can work. The plug can be a solid steel ball. The plug can be made of a malleable material such as foam or plastic that will deform under the force provided by the push rod and pass through the cannula but will press fit to the sides of the cannula when not under force. In this configuration, the end of the cannula does not need to be tapered because the plug deforms as it passes through the cannula. The length of the push rod can be such that the plug always dead ends at the distal end of the cannula but does not exit the cannula. The plug can be designed to fit over the push rod in a loose press fit such after delivery into the cannula, the force of the inner side wall of the cannula is greater than the loose press fit so that pulling the push rod from the cannula results in the plug remaining lodged within the cannula. In another configuration, the cannula can be tapered on the distal end, such that the plug is wider than the tapered end and therefore cannot exit the cannula.

Different configurations of the cannula and stylet are contemplated. For example, the cannula can be made from steel, laser cut steel to add flexibility, plastic such as PEEK, or a combination of any of the above. Laser cutting steel and shrink wrapping peek over steel is a well-known manufacturing process in the industry. Also, manufacturing a steel reinforced plastic cannula is a well-known capability in the industry. Examples include coil reinforced composite tubing and braid reinforced tubing manufactured by Duke Extrusion Inc., Santa Cruz, Calif.

The side aperture and plug described above can be used for a purpose other than aspirating marrow. The side aperture on the cannula can be shaped like an elongated slot (as opposed to a circular hole, which is a preferred configuration for aspirating marrow or delivering a substance). This slot can be cut along the length of the cannula (as opposed to across the cannula) so that the center of the slot is perpendicular to the handle. The plug can have a sloped shape on the proximal end (near the handle) and a blunt shape on the distal end (near the open hole at the end of the cannula). The plug is inserted into the cannula with the orientation of blunt end first. The push rod can be used to insert the plug. The sloped part of the plug can, upon insertion into the cannula, be aligned to run parallel to the handle of the push rod and the slot in the cannula. The length of the push rod can be such that it delivers the plug into the cannula at a depth equal to where the slotted side aperture is on the cannula. The taper on the distal end of the cannula can begin at a depth so that the plug lodges at a height parallel to the slot in the cannula. By aligning both the handle of the cannula with the handle of the push rod, the sloped part of the plug can be made to align with the side aperture of the cannula. The higher end of the slope of the proximal end of the plug can be opposite to the slot in the cannula and the shorter end of the sloped plug can be next to the slot. When the cannula taper and aperture and the plug is configured in this manner, it allows for a second, longer cannula, solid rod, guide wire, or screw to be inserted through the cannula and out of the side aperture at an angle determined by the length of the slot and the angle of the plug. Various angles for the plug and lengths of the slot and cannula are contemplated. The second cannula, rod, wire, or screw that exits through the aperture at an angle can be made of various suitable materials and can be attached to a handle.

The same features described above for aspiration of marrow can be used to deliver material only through the side aperture.

Embodiments of the present invention minimize influx of peripheral blood during the marrow aspiration process by sealing the distal opening of the cannula and forcing aspiration through the side aperture(s) only. Embodiments also allow for directional delivery of fluids and directional insertion of an instrument, e.g., a second cannula, wire, or rod, at a pre-determined angle into tissue, e.g., bone.

Thus, there is disclosed an aspiration device including an outer hollow cannula secured in a handle, the outer cannula defining a distal tip that is tapered and includes a distal opening; a stylet designed to be inserted in the outer cannula, the stylet defining a sharp distal tip; and a plug designed to be inserted in the outer cannula. One or more side apertures are defined in a side of the hollow cannula. When the plug is inserted into the hollow cannula, the plug forms a press fit distal to the side aperture so that fluid communication is maintained with the side aperture(s) but the distal opening at the end of the cannula is closed off, thus forcing the aspiration into the side apertures only. A key safety benefit of this novel configuration is that one can advance the cannula forward and aspirate through the side aperture(s) only without danger of having the plug being left behind in the body because all the force is to push the plug further back into the cannula.

There is further disclosed an aspiration device including a hollow cannula secured in a housing or handle that has a Luer connector and is configured to be coupled with a sharp stylet receivable in the cannula. The cannula defines an end hole (e.g. a distal opening) and one or more side apertures. A deformable plug made of plastic or foam is provided. The outer dimension of the plug can be greater than the inner dimension of the cannula. The deformable plug can be forced down the cannula by the assistance of a push rod. The push rod can be of a length such that it cannot push the plug out the end of the cannula. The push rod can be of a length such that the plug is deployed near the distal end of the cannula. The deformed plug creates a press fit inside the cannula and seals the end hole. The plug seals the end hole proximal to the side aperture or apertures in the cannula. In this configuration, the side apertures are in fluid communication with the Luer fitting and the distal end of the hollow cannula is closed off by the plug, thus forcing fluid into the side holes when a vacuum is applied via the cannula.

There is further disclosed a device including an outer cannula secured in a handle; a stylet designed to be inserted in the outer cannula, the outer cannula being tapered on the distal end, the outer cannula having a side aperture shaped like an elongated slot running up the length of the cannula; and a plug that is blunt at one end and tapered at the other end. A push rod is configured to align and deliver the plug into the hollow cannula such that the proximal, sloped end of the plug is parallel to the slot in the cannula and the distal, blunt end of the plug forms a press fit against the tapered inner wall of the cannula. The higher end of the sloped plug is across from the slot in the cannula and the lower end of the plug is next to the slot in the cannula. An instrument, such as a rod, screw, wire, or another cannula, can be inserted through the cannula having the side aperture such that the instrument deflects along the slope of the sloped plug and exits the side aperture at a predetermined angle.

There is further disclosed a method for aspirating bone marrow or delivering fluid or advancing an instrument (e.g., a rod, screw, second cannula, drill, catheter, etc.) through a side aperture of a first cannula where the end of the first cannula has been sealed off with a plug that is inserted after the stylet, which is used for insertion into bone, is removed.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 10A-10D illustrate an embodiment of a bone access device including a slanted plug that is receivable in a first cannula having a slot-shaped side aperture. A second cannula can be inserted through the first cannula and is directed to exit the first cannula through the side aperture at an angle to first cannula.

FIGS. 11A-11D illustrate use of the device of FIG. 1 to aspirate bone marrow.

DETAILED DESCRIPTION

A description of example embodiments follows.

Bone marrow aspiration devices including an introducer cannula and an aspiration cannula are described in International Application No. PCT/US2010/036696, filed on May 28, 2010 and published on Dec. 2, 2010 as WO2010/138895 A2, and International Application No. PCT/US2013/067358, filed on Oct. 29, 2013 and published on May 8, 2014 as WO2014/070804 A1, the teachings of which are incorporated herein by reference in their entirety.

A bone marrow aspiration device and associated method including an introducer needle assembly, an aspiration needle assembly and a depth guide that includes a screw assembly are described in International Application No.: PCT/US2015/011614, filed on Jan. 15, 2015 and published on Jul. 23, 2015 as WO2015/109100 A1, the teachings of which are incorporated herein by reference in their entirety.

A bone marrow aspiration device and method including an introducer cannula, an aspiration cannula and a mechanism (e.g., a screw assembly) to move the cannulae are described in U.S. application Ser. No. 14/885,821, filed on Oct. 16, 2015 and published on Apr. 21, 2016 as US 2016/0106462 A1, the teachings of which are incorporated herein by reference in their entirety.

Prior bone marrow aspiration devices include an inner aspiration cannula and an outer introducer cannula. In these devices, a distal end of aspiration cannula closes the distal opening of the introducer cannula. To avoid air leaking in between the cannulae, a connector is provided to couple the inner cannula to outer cannula in an air-tight manner. Certain embodiments of the present invention only include a single aspiration cannula and, consequently, do not encounter an air leakage problem. Instead of using an inner cannula to close the distal opening of the outer cannula, a plug is provided to seal the distal opening of the single aspiration cannula. Aspiration is through side holes in the cannula.

A typical marrow biopsy needle includes a tapered distal end and a distal opening to core a marrow sample (marrow dowel) from bone. The bone sample tends to swell when pushed into the lumen of the needle. The tapered end helps retain the marrow sample within the lumen of the needle when retrieving the needle from bone. Such a biopsy needle does not include side holes. Add side holes would make it difficult to remove the bone sample from the biopsy needle.

Figure 1:
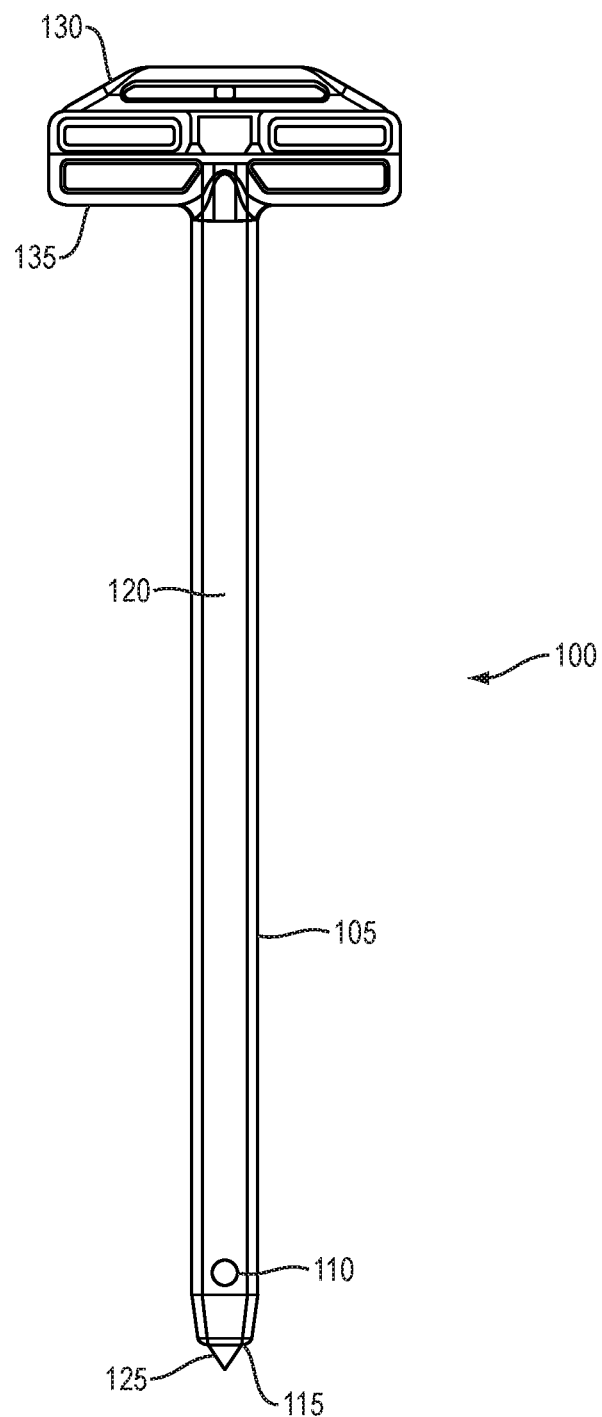
FIG. 1 is a side view of an example bone access device showing a sharp stylet with a handle assembled into a cannula with a handle, the cannula having side aperture distal to the handle.

Referring first to FIG. 1, a bone marrow access device 100 in accordance with the principles of the present invention includes a cannula 105 defining a side aperture 110 and a distal opening 115. A stylet 120 defines a sharp distal tip 125 and is receivable in the cannula. The stylet includes a handle 130 and assembles into the cannula which also has a handle 135. The cannula handle and stylet handle can interlock so that the cannula and stylet can be positioned in bone as one unit. The cannula 105 can be permanently secured at a proximal end to the cannula handle 135.

Figure 2:
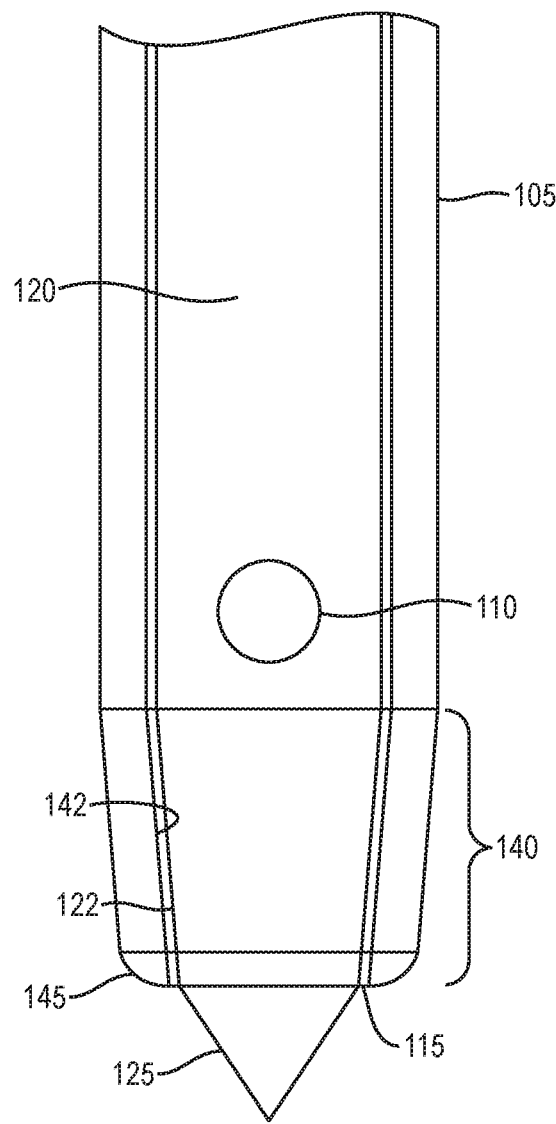
FIG. 2 is a detailed view of the distal tip of the cannula of FIG. 1 with the sharp stylet extending beyond the end of the cannula and an aperture above the tapered end of the cannula distal to the sharp point of the stylet.

As shown in FIG. 2, the distal tip 145 of the cannula is tapered 140 and defines the distal opening 115. At least one side aperture 110 is on a side of the cannula above the taper 140 on the distal end. The tip of the cannula is preferably designed of a hard material to withstand the forces applied when penetrating through the cortex of the bone. The sharp stylet 120 extends beyond the tip of the cannula to assist in penetrating bone. The stylet 120 is preferably designed of a hard material to withstand the forces applied on the stylet when penetrating through the cortex of the bone. A suitable material is stainless steel. The stylet 120 also functions to support and stiffen the cannula 105. Thus, flexibility designed into the cannula 105 can be overcome for the purpose of penetrating the hard cortical bone by relying on the stylet 120 to stiffen and support the cannula. Once through the hard cortex, a different stylet that is less stiff can be deployed to allow the cannula 105 to pass through trabecular bone which is not as hard as the cortex. The combination of the less stiff stylet and flexible cannula will allow the cannula to bend as it passes through trabecular bone along the inner contours of the bone. For example, laser cutting a steel cannula and shrink wrapping a thermoplastic polymeric material, such as polyether ether ketone (PEEK), over the steel cannula is a well-known manufacturing process in the industry that can make a cannula flexible. Also, manufacturing a steel reinforced plastic flexible cannula is a well-known capability in the industry.

Figure 3:
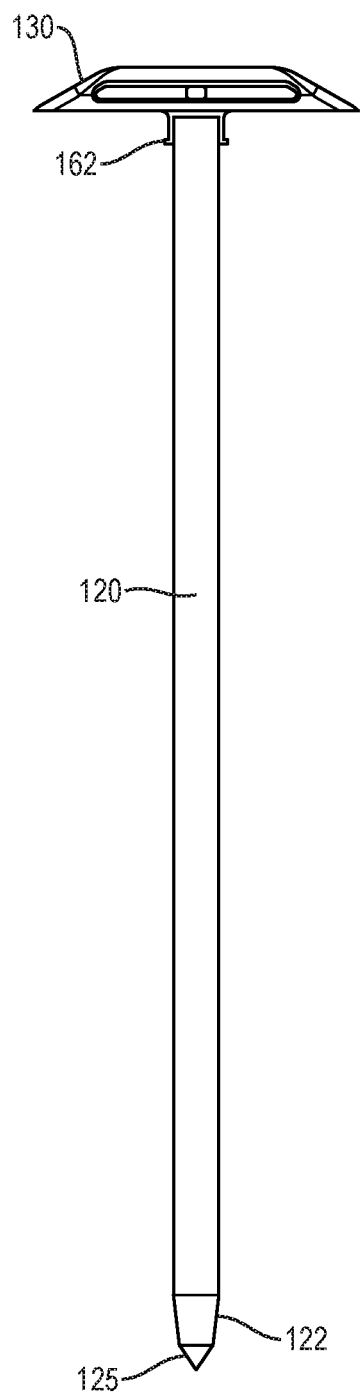
FIG. 3 is a side view of the sharp stylet of the device of FIG. 1.
Figure 4:
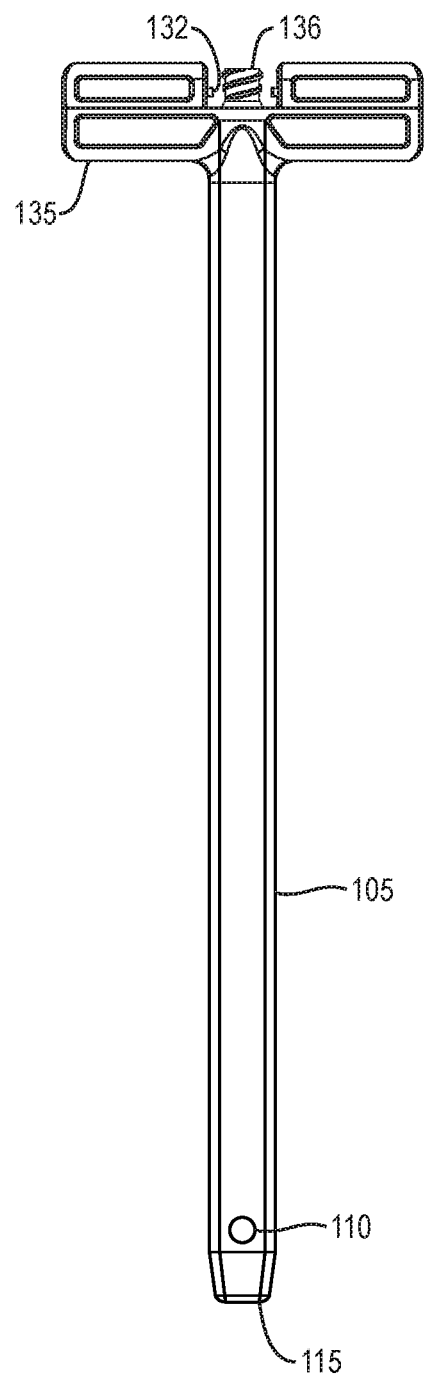
FIG. 4 is a side view of the cannula of the device of FIG. 1 with stylet of FIG. 3 removed, illustrating the center Luer hub connector and side aperture on the side of the cannula.

FIG. 3 is a side view of the sharp stylet 120 of the device of FIG. 1. As mentioned, a proximal end of the stylet 120 includes a stylet handle 130. The stylet handle is configured to secure the stylet handle within the handle 135 attached to the cannula, as shown in FIG. 1. To this end, as shown in FIGS. 3 and 4, the stylet handle 130 has features, such as tabs 162, which interlock with complementary features, such as slots 132, at the cannula handle 135. Securing the stylet handle 130 to the cannula handle 135 when the stylet is inserted through the cannula prevents the stylet from rotating while penetrating the bone cortex. The stylet can include a tapered outer surface 122 that is complimentary to the tapered inner surface 142 (FIG. 2) of the cannula 105.

FIG. 4 is a side view of the cannula of the device of FIG. 1 with stylet of FIG. 3 removed, illustrating the center Luer hub connector 136 at cannula handle 135 and the side aperture 110 of the cannula 105.

Returning to FIG. 1, the stylet 120 is adapted to be secured within the outer cannula 105 in order to penetrate the bone cortex. Thus, the outer diameter of the stylet 120 is slightly smaller than the inner diameter of the outer cannula 105. When the stylet is inserted into the outer cannula and the stylet handle is secured in the cannula handle, the sharp distal tip 125 of the stylet extends slightly beyond the distal tip 145 of the outer cannula as illustrated in FIG. 2. Thus, the sharp distal tip 125 of the stylet works in conjunction with the distal tip 145 of the outer cannula 105, which can include sharp, cutting edge, to assist in penetrating the bone cortex.

Figure 5:
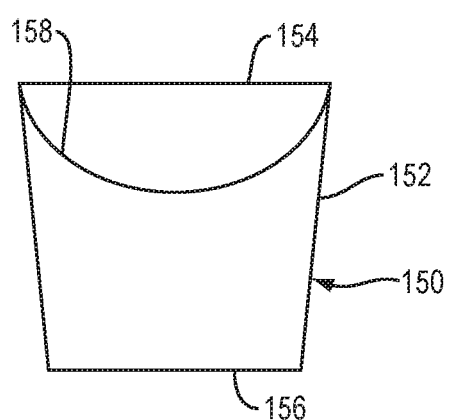
FIG. 5 is a side view of an example plug that can be press fit into the tapered end of the cannula of FIG. 4. The outer dimension of the widest part of the plug is greater than the inner dimension of the tapered end of the cannula.
Figures 7A, 7B:
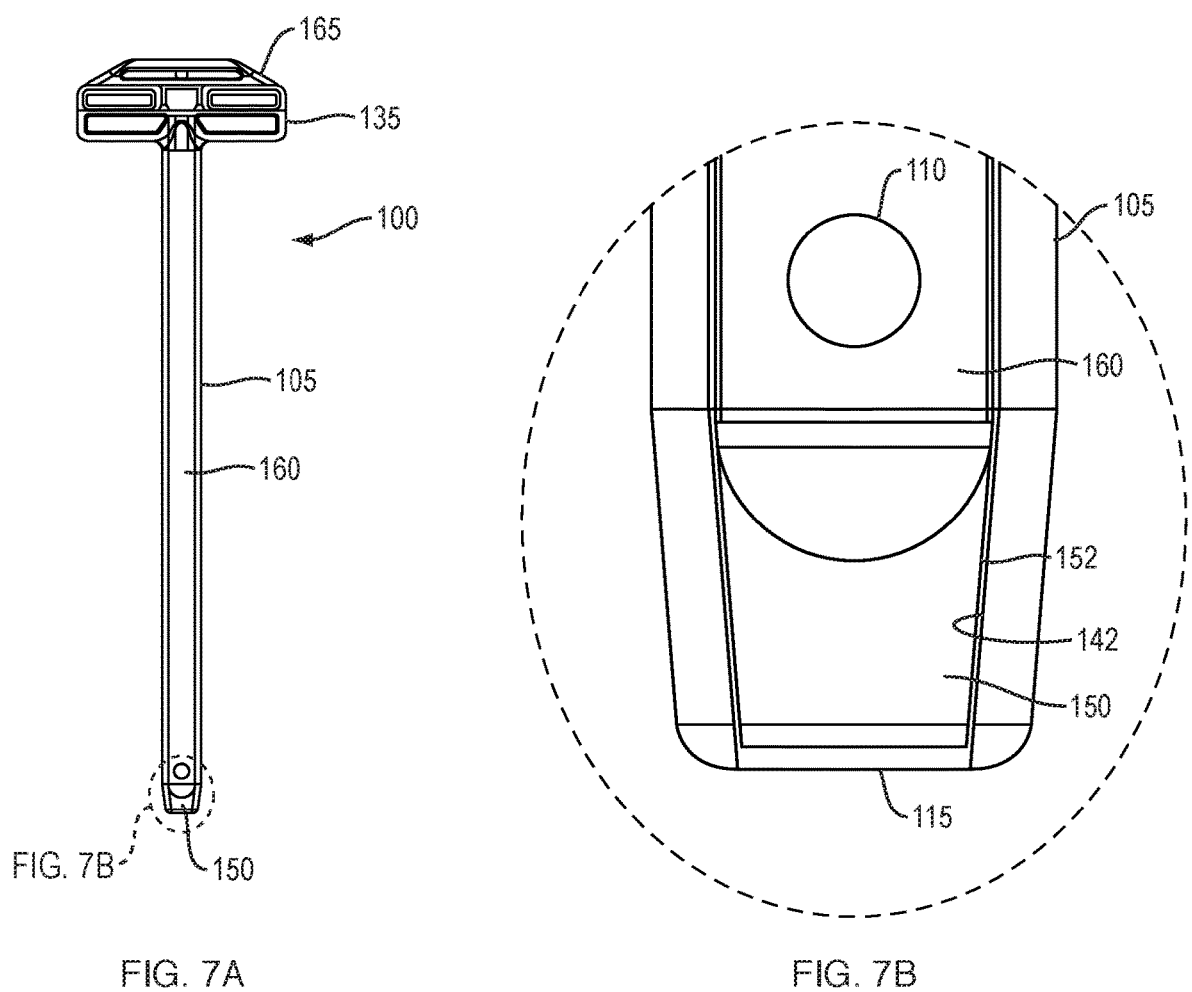
FIG. 7A is a the side view of the device illustrating the view of the push rod fully extended into the cannula such that the plug is secured in the taper distal end of the cannula below the side aperture.
FIG. 7B is a detailed view of the distal end of the device in FIG. 7A.

The bone marrow device in accordance with the principles of the present invention also includes a plug to be deployed into the cannula once the stylet has been removed. An example plug 150 is shown in FIG. 5. In a preferred embodiment, an outer dimension of the plug is less than the inner dimension of the cannula on the proximal end near the handle but is greater than the inner dimension of the cannula at the distal end where the cannula begins to taper. The plug includes a proximal end 154 and a distal end 156, the proximal end being wider than the distal end. As shown in FIG. 5 and FIG. 7B, an external surface 152 of the plug is tapered to complement the tapered internal surface 142 of the cannula. The distal end 156 is blunt, to seal the distal opening 115 of the cannula.

Figure 6:
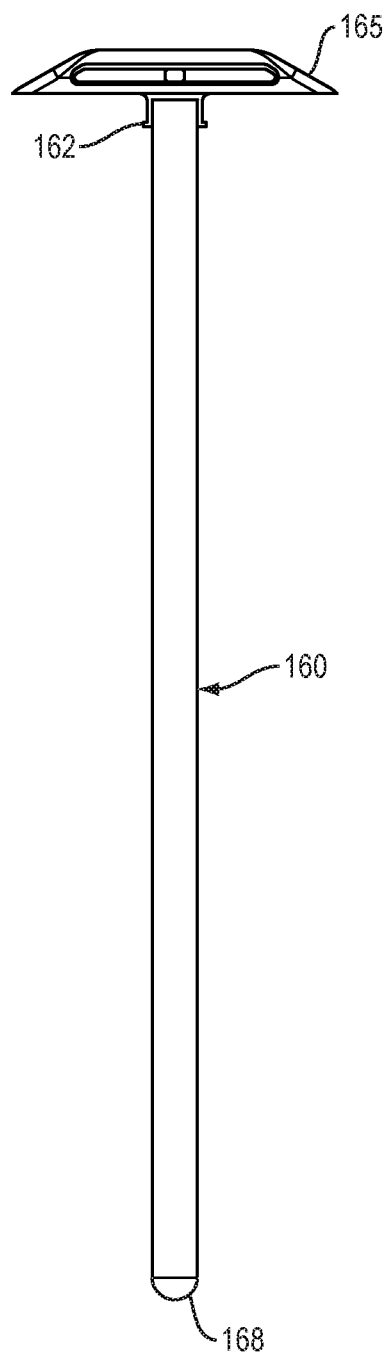
FIG. 6 is a side view of a push rod with a handle that can be used to advance the plug through the cannula to the distal end where the plug hits the tapered inner surface of the cannula.

The bone marrow device made in accordance with the principles of the present invention can also include a push rod that can be used to push the plug down the inner lumen of the cannula until the plug lodges inside the tapered end. An example push rod 160 is shown in FIG. 6. The length of the push rod 160 can be such that it pushes the plug 150 a pre-determined distance, such as just past aperture 110 on the side of the cannula 105, as illustrated in FIGS. 7A-7B. The outer diameter of the push rod 160 is generally less than the inner diameter of the cannula 105. The push rod 160 can be flexible and have different diameters along its length. The push rod can have a handle 165 that is configured to be easily grasped by the user, to facilitate insertion of the push rod into the cannula. The handle can be configured to butt against the cannula handle, to thereby provide a positive stop in order to limit length of insertion of the push rod into the cannula. As shown in FIG. 6, handle 165 can be configured to mate with the cannula handle 135 in the same manner as the stylet handle 130 mates with the cannula handle.

A distal end 168 of the push rod 160 can be configured to interface with the proximal end 154 of the plug. The plug and the push rod may define complementary features (158, 168). For example, the distal end of the push rod 160 can be convex and the proximal end of the plug can be concave 158 (FIGS. 5, 6). The push rod 160 may be partially receivable in the plug 150, the plug capping the distal end of the push rod, as shown in FIG. 7B (see also FIGS. 13A-13B).

Figure 8:
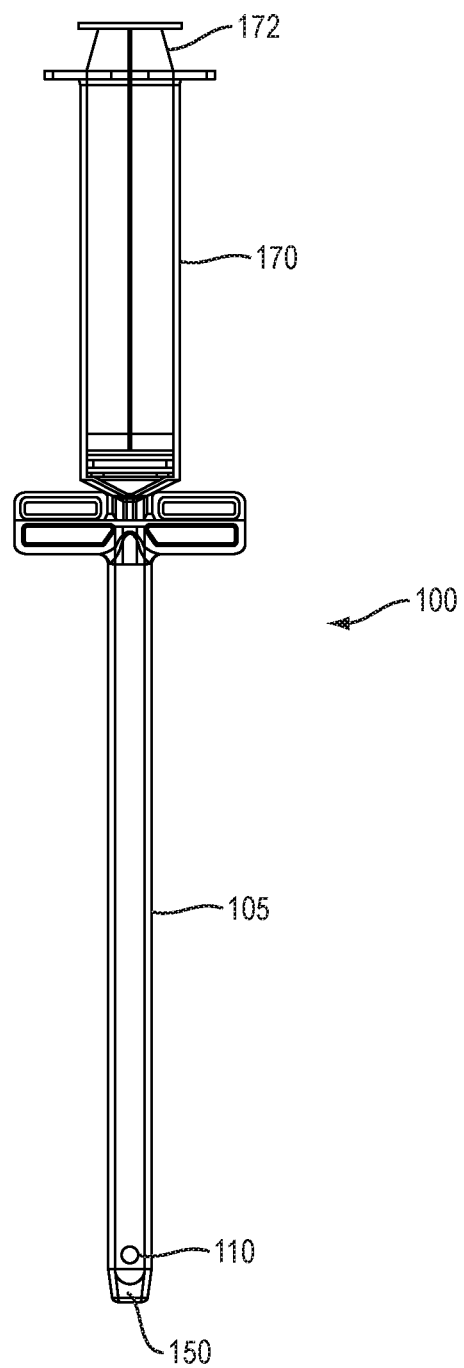
FIG. 8 is a side view of the device illustrating the sharp stylet and push rod removed, with the plug lodged into the taper of the cannula below the side aperture and a syringe connected to the Luer hub of the cannula handle.
Figure 9:
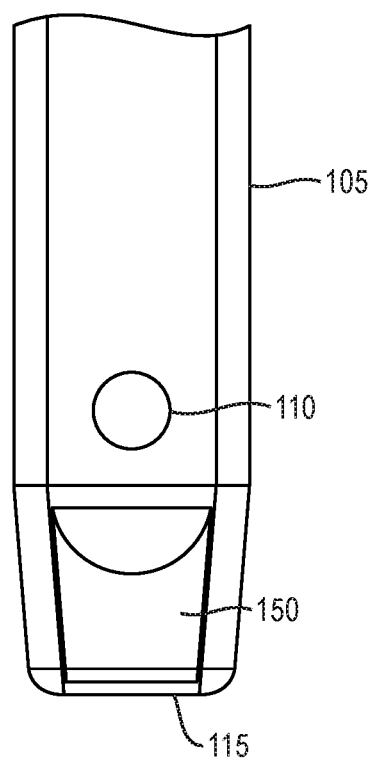
FIG. 9 is a detailed view of the distal end of a cannula of FIG. 8 with plug secured in the taper below the aperture.

As illustrated in FIG. 8, the bone marrow device 100 in accordance with the principles of the present invention also includes a syringe 170 that attaches to the Luer hub connector 136 on the handle 135 of the cannula once the stylet 120 and push rod 160 have been removed and the plug 150 has been inserted and press fit into the taper 140 of the cannula past the aperture 110. FIG. 9 shows a detailed view of the plug 150 sealing the distal opening 115 of the cannula 105. Pulling on the plunger 172 of the syringe 170 creates negative pressure and results in fluid flow through the one or more side apertures 110 as the end of the cannula 105 has been sealed by the plug 150.

Aspiration sources that can be used include any aspiration source having a component that can couple to the proximal end or attachment structure of the device, e.g., via a Luer connector 136, and effect the withdrawal of marrow from bone. Suitable aspiration sources include, but are not limited to, vacuum sources and associated tubing, siphons, syringes (as shown in FIG. 8), and the like.

As exemplified in FIGS. 10A-10D, a bone marrow device in accordance with the principles of the present invention can include an aperture 210 that is shaped like a long slot and a plug 250 that is sloped (slanted) on one end and blunt on the other end. FIG. 10A illustrates the slot shaped aperture 210 above the taper 240 on the distal end of the cannula. As shown in FIG. 10B, the sloped plug 250 includes a sloped end 254 and a blunt end 256. The plug is inserted into the cannula 205 blunt end first. The blunt end 256 of the plug seals the distal opening 215 of the cannula and forms a press fit against the tapered inner wall 242 of the cannula, as illustrated in FIG. 10C. The sloped end 254 of the plug 250 is opposite the blunt end 256 and closest to the cannula handle 235 at the proximal end of to the cannula. A push rod (e.g., push rod 160) can be used to deliver the plug 250, whereby the push rod is inserted into the cannula 205 from the proximal end to push the plug distally. The push rod can be cut to a length to deliver the plug so that the lower end of the slanted plug is aligned with and next to the bottom of the side slot, near the distal end of the cannula, and the upper end of the slanted plug is aligned with the top of the slot, nearest to the cannula handle. The upper sloped end of the plug is across from the side slot such that when the plug is in place, it leaves the slot 210 open as shown in FIG. 10C. Inserting an instrument 280, such as a second, longer cannula, into the first cannula will result in the second cannula exiting the side slot 210 at an angle $\alpha$ to the first cannula that is based on the angle of the slope of the plug 250 and the length of the side slot 210. The angle $\alpha$ can be in the range of about 25 to about 75 degrees, preferably about 35 to about 70 degrees, and more preferably about 45 to about 60 degrees. In one example, the angle is about 45 degrees. In another example, the angle is about 60 degrees.

Although the sloped plug 250 as illustrated in FIGS. 10B-10D includes a linearly sloped surface 258, the slope can be curvilinear. Furthermore, the sloped surface 258 of the plug need not be flat but can be curved. For example, the sloped surface 258 can be shaped to guide the distal tip 282 of an instrument that is inserted through the cannula in order to deflect the instrument from a straight path. In general, the slope surface can be configured to direct an instrument 280 inserted through the lumen of the cannula 205 from a direction substantially parallel to a longitudinal axis of the cannula to an axis that is at an angle $\alpha$ to the longitudinal axis. The angle $\alpha$ can be determined, at least in part, by the sloped surface 258 at the sloped end 254 of the plug.

Figure 11A:
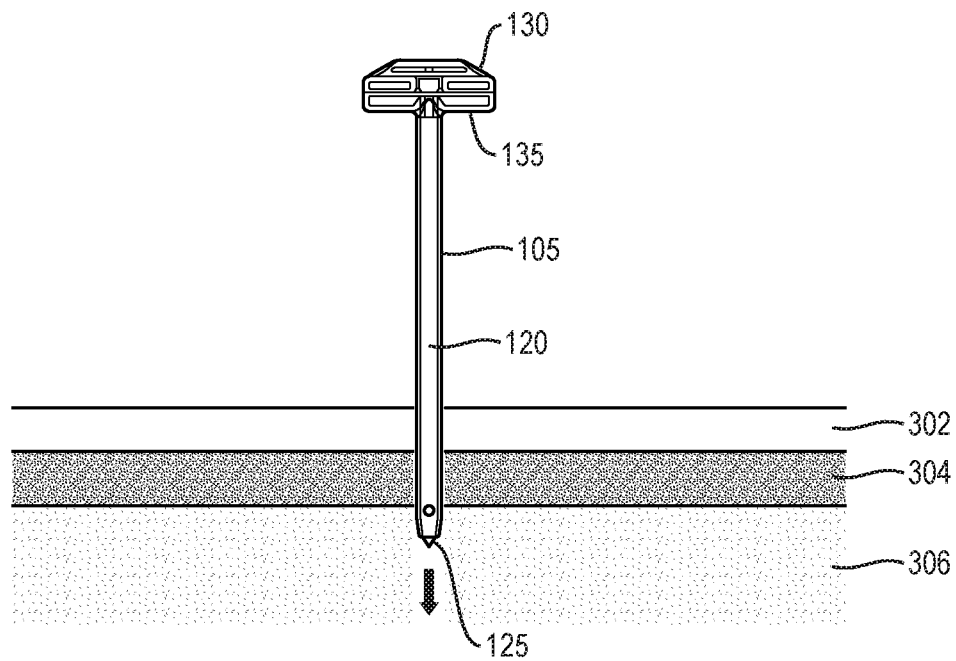
Figure 11B:
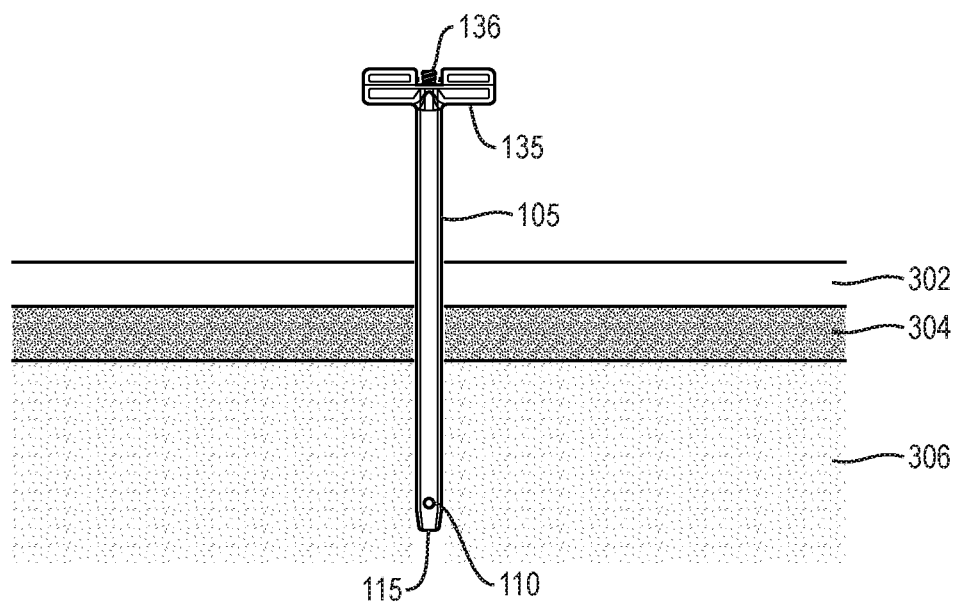
Figure 11D:
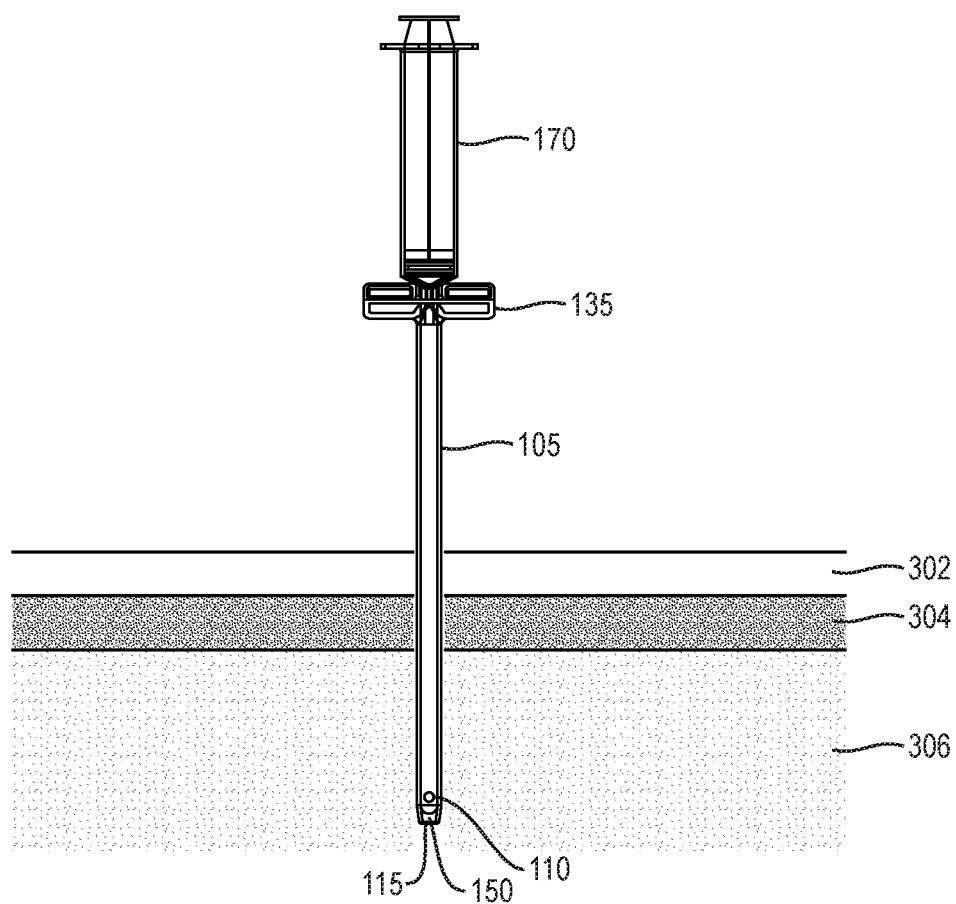

FIGS. 11A-11D illustrate use of a bone marrow access device 100 to aspirate bone marrow or deliver material into bone space of a patient in accordance with the principles of the present invention, which is now described. The patient has outer skin layers and a periosteum layer consisting of layers of soft tissue, shown collectively as layer 302, a hard cortex layer of the bone 304, and a medullar cavity 306, which contains the bone marrow. In use, the sharp stylet 120 is inserted into the outer cannula 105 and the stylet handle 130 is locked into the cannula handle 135. The health care professional then uses the sharp distal end 115 of the stylet and the sharp distal end of the cannula 105 to penetrate the outer layer 302 and bone cortex 304. Once the bone cortex has been penetrated to a depth so desired and the outer cannula is positioned in the medullar cavity 306, the stylet is removed, as shown in FIG. 11B. Next, as shown in FIG. 11C, the plug 150 is inserted into the cannula 105 past the aperture 110 using the push rod 160 until the plug lodges against the tapered part 140 of the cannula 105. The push rod is removed and a syringe 170 can be attached to the Luer hub in the cannula handle as shown in FIG. 11D. Negative pressure is applied via the syringe 170 and aspirate is pulled from the medullar cavity 306 through the side aperture(s) 110 and into the syringe, with the plug 150 plugging the end hole 115 of the cannula. Alternatively, a syringe filled with a substance, such as bone cement, can be used to deliver the substance directionally through the side aperture(s) only and not the end hole 115 of the cannula.

Use of a bone access tool made in accordance with the principles of the present invention is now described. In use, the sharp stylet is inserted into the outer cannula of the bone access tool and the stylet handle is locked into the cannula handle. The health care professional then uses the sharp distal end of the stylet and sharp distal end of the cannula to penetrate the bone cortex. Once the bone cortex has been penetrated to a desired depth and the outer cannula is in the medullar cavity, the stylet is removed. The procedure of inserting the cannula and stylet into bone is the same as illustrated and described above with reference to FIGS. 11A-11B. A plug (e.g., plug 250 of FIG. 10B) that is sloped on one end and blunt on the other is inserted into the cannula, blunt end first and distal to the cannula handle and the sloped end proximal to the handle. A push rod can be used to force the sloped plug into the cannula until the plug lodges against the tapered part of the cannula past the aperture. The slope of the plug aligns with the side slot of the cannula as shown in FIG. 10C. The higher part of the sloped plug is opposite to the slot and the lower part of the plug is next to the slot such that the slot remains open to the cannula after the plug is deployed. An instrument, such as a second cannula or guide wire, is inserted through the cannula and exists through the side slot after deflecting along the sloped plug. The slot and the sloped plug can be configured such that the instrument exits the cannula at a pre-determined angle as shown in FIG. 10D.

A plug and a push rod can be used with a flexible cannula. A portion or all of the cannula can be flexible.

Several methods and commercial versions of laser cut tubes are available in the market place. The cut pattern of such laser cut tubes is to make the tube flexible while also maintaining its strength against breaking or kinking. One such example is a product with the brand name FLEXMETRIC® provided by LenkBar, Naples, Fla.

Several bone marrow aspiration technologies are available on the market today. None of the current technologies use laser cut shafts to improve the flexibility of the aspiration cannula. This is because the cuts made to the steel of the cannula, in order to make it flex, allow air to leak through the cuts. Since air is a fluid that flows more easily than more viscous fluids (e.g., blood or marrow), such a cannula will draw only air.

Other approaches have tried to overcome this limitation by heat wrapping the cannula in TEFLON® material or otherwise covering the laser cuts with a flexible plastic that can adhere to the metal tube to keep the cuts air tight. However, the leading edge of such a covering, which is on the outside of the cannula, is not sharp or stiff enough to penetrate bone. In effect, as the cannula is advanced into bone, the outer covering tends to deform or roll up the cannula as opposed to penetrating the hard cortical bone. Such approaches have therefore been commercially unsuccessful. To overcome this limitation, one way is to make the cannula air-tight from the inside as described herein. In so doing, no deformable leading edge is created and the cannula can penetrate bone and also flex to follow the bone contour once inserted. The approach described here can improve the devices currently being sold under the brand name MARROW CELLUTION™, which are the subject of U.S. and foreign patent applications by the Applicant, including, for example, WO2015/109100 and US 2016, 0106462.

Figure 12:
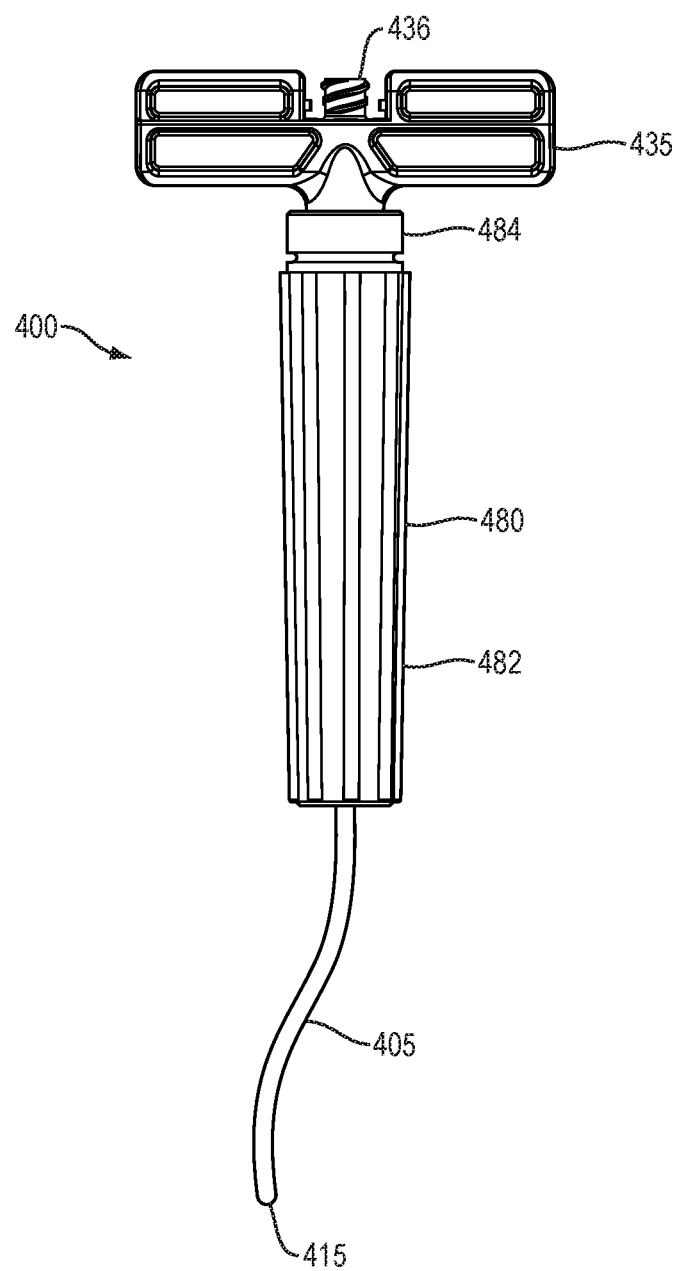
FIG. 12 is a side view of a bone marrow access device that includes a flexible cannula and a depth guide.

FIG. 12 illustrated a bone marrow access device 400 that includes a flexible cannula 405.

Because bone is very hard, the flexible cannula is preferably supported by a stiff stylet inserted into the cannula. The stylet can run along the length of the flexible cannula in order to support the cannula so that enough pressure can be applied to the cannula tip to allow the tip to be able to cut through, drill through, or otherwise penetrate cortical bone. The stylet can be sized to extend past the tip at the end of the laser cut cannula when assembled into the cannula, to substantially support the cannula along its length. The stylet makes the assembled cannula-stylet combination very stiff.

The laser cut portion of the aspiration cannula is made air-tight to allow for aspiration. A few different possibilities are available to accomplish this. First, the distal tip can have a larger diameter than the flexible, laser cut cannula so that the cannula can be heat shrunk with a plastic covering. Such plastic covering tends to not get caught on the bone cortical bone because the outer diameter (OD) of the tip and thus the hole made by the tip is equal to or greater than the OD of the combination laser cut cannula that is wrapped in heat shrunk plastic.

Another possibility is to place an inner cannula inside the flexible laser cut cannula that creates a seal at the distal end of the flexible cannula. The end of the flexible cannula has a solid tapered end. The inner cannula pinches against the taper of the laser cut cannula at the point of the taper. The press fit at the taper forms an air tight seal below the laser cuts. This method of making the two cannula air tight is described in more detail below.

Both single-cannula embodiments and dual cannula embodiments can employ various laser-cut tubing to make the cannula flexible. Several types of such tubing are available on the market.

The embodiment that includes an inner cannula and an outer cannula accommodates more easily the process of aspirating as the user moves the device back out (retracts) from the trabecular bone. The combination of an "introducer cannula assembly" and an "aspiration cannula" presents a novel solution to the problem of keeping a laser cut aspiration cannula airtight.

The cannula assembly 400 shown in FIG. 12 has a handle 435 with a Luer fitting 436. The handle is fitted with an adjustable depth guide (e.g., screw mechanism) 480. The cannula 405 incorporates a laser cut tube to make the cannula flexible. The cannula 405 defines a distal opening 415 and one or more side apertures (not shown).

Because bone is very hard, the flex cannula 405 is preferably supported by a stiff sharp stylet in order for the cannula to be able to initially penetrate cortical bone. The tip of the sharp stylet can protrude through the distal opening 415 at the distal end of the laser cut flexible cannula 405. After penetrating the cortical bone, the sharp stylet can be removed and another stylet can be inserted in its place. This stylet can be blunt tipped. The blunt tipped stylet can also have a different stiffness, e.g., it can be much less stiff than the sharp stylet. This difference in stiffness allows the laser cut cannula 405 to flex more inside the medullary space when the blunt stylet is used. Because the tip of the cannula is tapered, the blunt and sharp stylet can have a narrower OD at the bottom to better allow the distal end of the stylet to fit the profile of the taper of the laser cut tube while also, in the non-tapered portion of the cannula, minimizing the distance between the inner diameter (ID) of the length of tube that is laser cut to the OD of the stylet. This change in OD can look similar to a wedding cake tiered structure.

Once the laser cut flexible cannula ("introducer cannula assembly") has penetrated the cortical bone with the sharp stylet in place, and then deeper into the medullary space of the trabecular bone with the blunt stylet in place, aspiration can begin. The blunt stylet is removed at this point.

To get high cell counts, one preferably wants to close the distal opening 415 of the laser cut tube from the introducer cannula assembly and configure it so that no air leaks through the laser cuts and into the aspiration syringe. To accomplish this, one can put a jacked on the cannula to seal the laser cuts, and place a plug to seal the distal opening, as described herein. Alternatively, a second, aspiration cannula can be inserted into the introducer cannula assembly. This aspiration cannula has an outer jacket designed so that it can pass through the lumen of the laser cut tube before the taper, but becomes lodged when it comes into contact with the tapered end of the laser cut tube. The material of the jacket can be TEFLON® (or other suitable material), and such material can be heat treated so that it is firmly in place on the aspiration cannula. The metal tube under the TEFLON® shrink wrap can also have laser cuts to make it flexible and thus be more easily able to contour to the laser cut tube of the introducer cannula assembly when they are coaxially fitted together. The jacket preferably has some degree of deformity. The bottom of the cannula has a window cut out of it so that when the handles of both cannulas are parallel, the window aligns with the side aperture at the tapered distal end of the laser cut tube. The end of the aspiration cannula is blunt and solid. It is designed to close off the opening at the end of the laser cut tube. Thus, with the window aligned and an air tight seal at the interface to the deformable jacket and the taper of the introducer cannula, aspiration is primarily from the side aperture of the laser cut tube.

The aspiration cannula can come with an optional solid stylet to add stiffness. This solid stylet fits into the cannula and attach to the handle in the same fashion as the stylet of the introducer cannula assembly previously described.

The depth guide 480 includes a screw set (e.g., a screw assembly including a threaded jacket 482 and a lead screw 484 receivable in the threaded jacket) that can be used as previously described in other patent applications by the Applicant, including, for example, WO2015/109100 and US 2016/0106462. Using the patient as leverage, the screw set can be used to remove the needle from bone by turning the introducer handle counter clockwise while holding the depth guide. The depth guide can provide for controlled retrieval of the cannula from bone. Marrow can be aspirated as the cannula is retrieved.

Figure 13A:
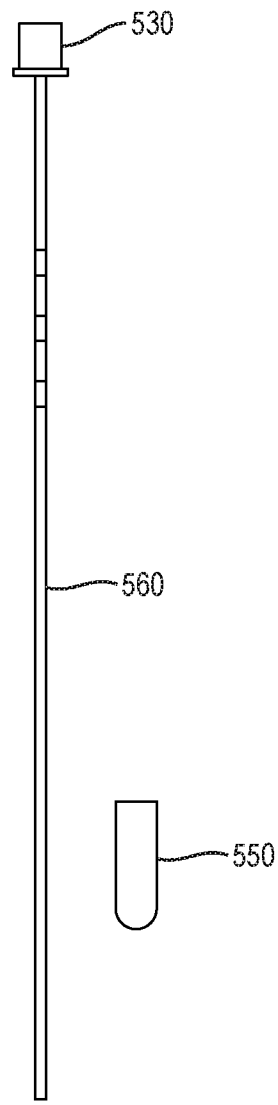
FIGS. 13A-13B illustrate a cap-shaped plug and a push rod to deliver the plug.
Figure 13B:
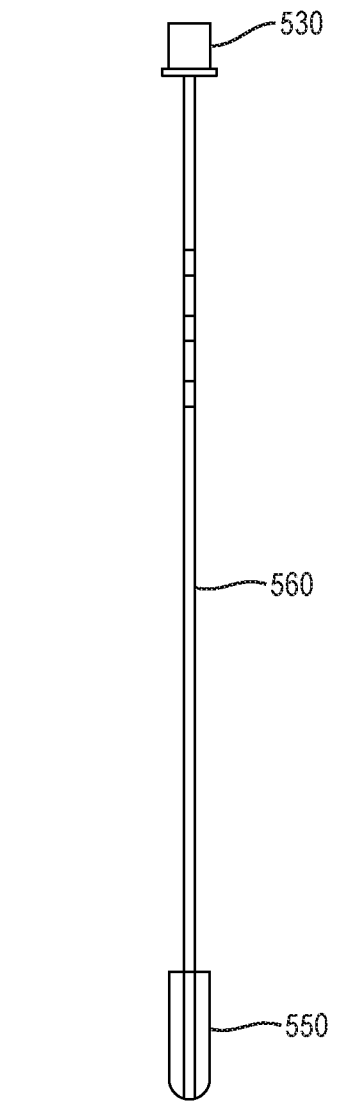

FIGS. 13A-13B illustrates a push rod 560 and a cap-shaped plug 550. The plug slides over the distal end of the push rod 560 as shown in FIG. 13B. The push rod with the cap-shaped plug fitted over the distal end fits through the Luer connector into the hollow aspiration cannula when the stylet has been removed. The push rod includes a handle 530, which, as illustrated, can be small, knob-shaped, and need not have wings. The handle 530 can butt against the cannula handle, to limit the distance the push rod can be inserted into the cannula. A useful feature of this design is that when the push rod is inserted into the cannula, the plug on the end of the push rod is positioned at the end of the aspiration cannula below the one or more side apertures of the cannula. The push rod is then removed leaving behind the plug. With the plug deployed this way, the side apertures remain open and the distal opening of the cannula becomes closed. The push rod has an exact length so that the plug cannot be pushed out the end of the cannula but always resides just at the distal end of the cannula. As described above, the distal end of the aspiration cannula can be tapered to create a press fit for the plug.

It can be appreciated that other types of plugs can be loaded into the aspiration cannula with the push rod in order to form the seal at the distal end of the aspiration cannula. Example plugs having various shapes and sizes are presented in FIGS. 14A and 14B. The choice of plug used can depend on the location of the side aperture(s) and the configuration of the distal end of the cannula, e.g., whether the distal end is tapered or not.

Figure 14A:
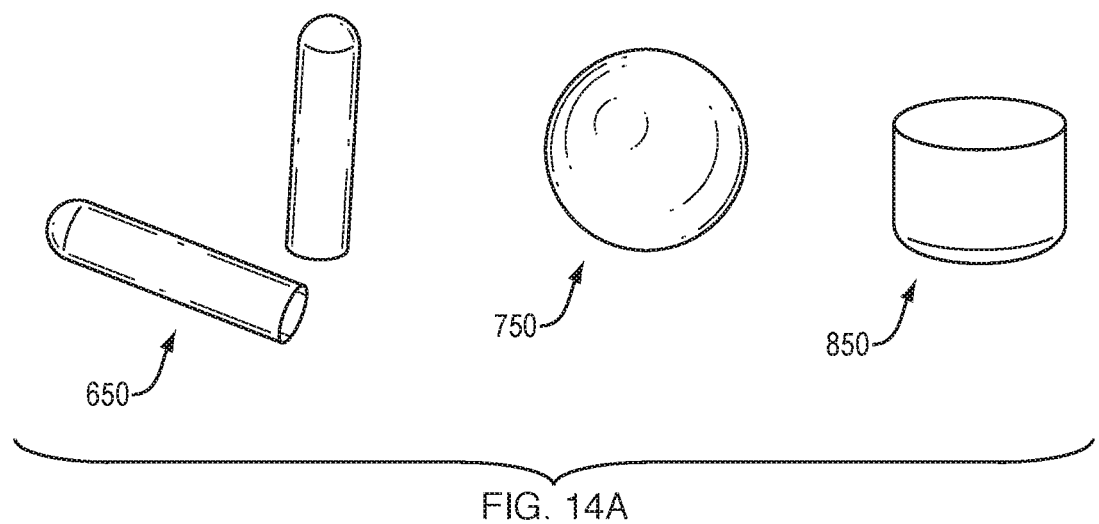
FIGS. 14A-14B illustrate example plugs that can be used with embodiments of the invention.

As shown in FIG. 14A, plugs 650 are cap-shaped and are characterized by an elongated body, a proximal opening, and a rounded, distal end. Plug 750 is a ball. Plug 850 is again cap-shaped, but shorter and wider than plug 650. Different lengths, widths, and materials can work for different applications.

Figure 14B:
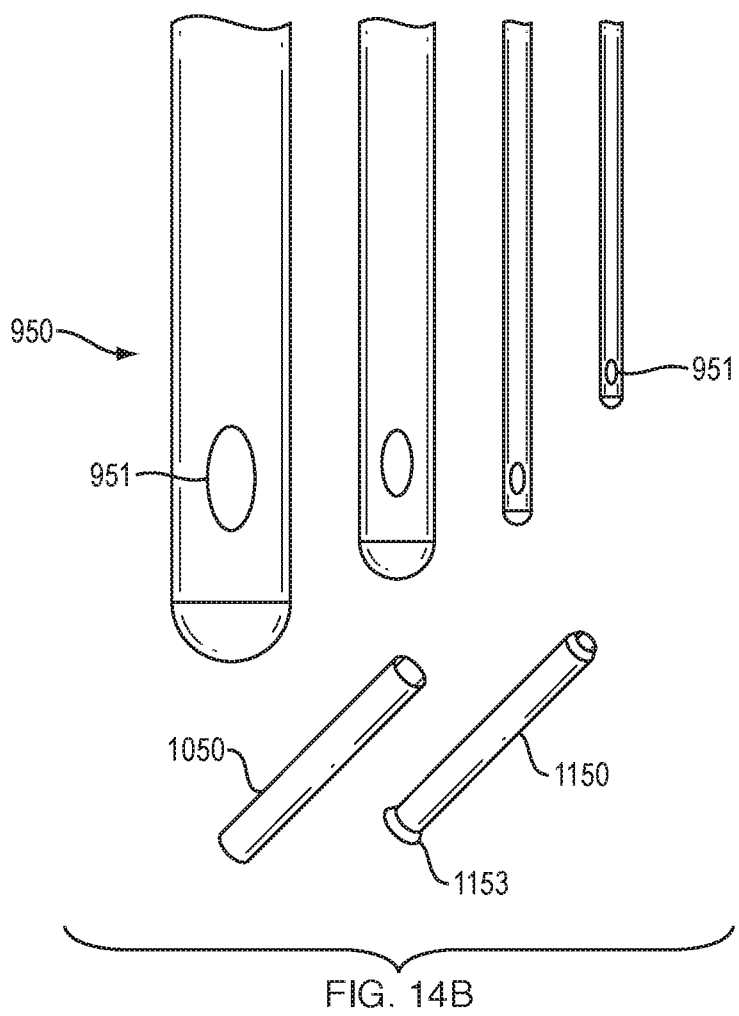

As shown in FIG. 14B, plugs 950 are elongated tubes of different diameters and each with a closed, distal end. Each plug 950 includes an opening 951 in a side of the plug. The opening communicates with a lumen in the plug. Plug 1050 is cylindrical, the distal end being flat. Plug 1150 is also substantially cylindrical, but the proximal end includes a flange 1153 that aides in lodging the plug again an inner surface of the cannula, e.g., tapered inner surface 142 (FIG. 2).

If the length of the plug extends on the inside of the cannula beyond the side apertures, a cut out or other opening can be provided in the plug, such as cut out 951 shown in FIG. 15B. The cut out is configured to align with the side aperture(s) of the cannula and that is in fluid communication with the lumen of the cannula proximal to the plug. Aspiration of marrow or delivery of a substance can be accomplished through the side aperture(s) and the cut out in the plug.

The plug is a sealing mechanism to seal the distal opening of the cannula. The sealing mechanism can be made of closed cell foam, plastic or other deformable material to better create the press fit at the end of the cannula. In addition, the plug can be very long with a cutout to line up with one or more of the side apertures of the cannula. After deployment, the plug can span the entire length of the cannula with one end being inside the upper handle or Luer connector at the cannula handle. The long tube could be long enough to fit over, into or be otherwise attached to the syringe male Luer tip (i.e., the Luer tip of the syringe tube of the syringe could be several inches long, for example, 5 or more inches).

So, by way of example, the tip of the syringe proximal to the plunger handle, can be extended and made to be closed ended and have one or more side holes, thereby forming a tubular "plug" to seal the distal opening of the cannula. After deployment, at the distal end, the plug that has been incorporated into the syringe seals the distal opening of the cannula; at the proximal end, the plug seals the Luer connector port. The length of the cap could be so long that it could be placed inside the aspiration cannula without the need of the pusher rod because it is attached to the syringe. The embodiment described can be used for both aspiration and infusion of material.

Figure 15:
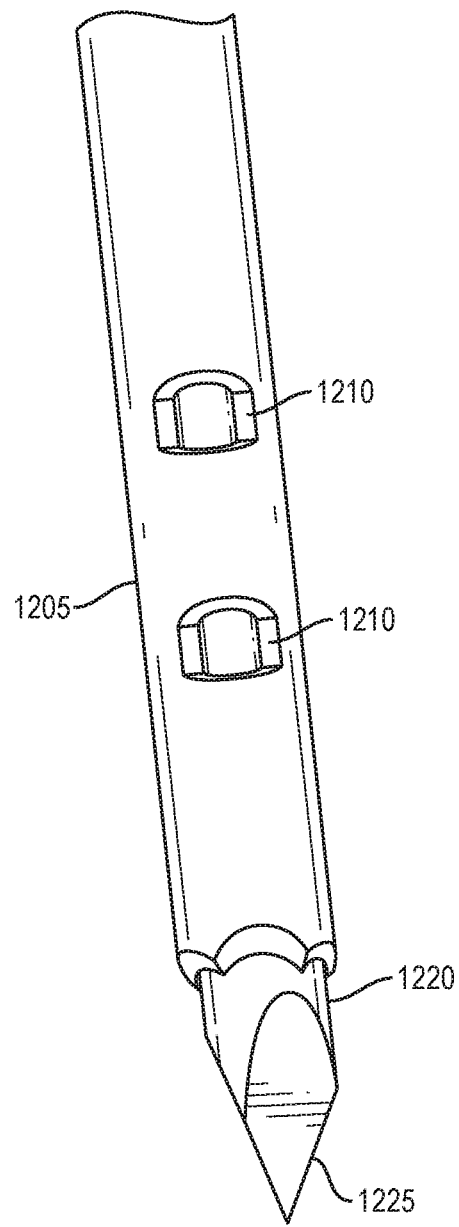
FIG. 15 is a perspective view of the distal end of a cannula with a sharp stylet according to an example embodiment of the invention.

FIG. 15 shows an example of a stylet 1220 assembled into an aspiration cannula 1205 according to an embodiment of the invention. The cannula 1205 includes two side apertures 1210 near the distal end of the cannula. The stylet 1220 includes a sharp distal tip 1225 that extends beyond the distal end of the cannula. Once the stylet 1220 is removed, any suitable plug described herein can be used with the cannula 1205 to seal the cannula's distal opening. It will be understood that a push rod or blunt stylet can be used to position the plug in the cannula. Other forms of sealing the distal opening of the cannula while leaving at least one of the side apertures 1210 open are also contemplated, as described herein.

Thus, embodiments of the present invention meet a long-felt need in the medical community that has not been met by others to provide an aspiration device that is able to aspirate a sample while minimizing peripheral blood. Embodiments also allows for directional delivery of another cannula or other instrument, such as a guide wire, through the side aperture of the cannula.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:
1. A bone marrow access system comprising:
   a cannula defining a distal opening at a distal tip of the cannula and a side aperture in a side of the cannula and positioned proximally from the distal opening, the cannula including a tapered internal surface near the distal tip of the cannula;
   a sharp stylet removably positioned in the cannula, the stylet having a sharp distal tip and extending beyond the distal opening;

a plug receivable in the cannula distal to the side aperture to seal the distal opening of the cannula when the sharp stylet is removed, the plug configured to securely lodge against the tapered internal surface of the cannula; and a push rod separate from the plug and receivable in the cannula to deploy the plug into the cannula to seal the distal opening.

2. The system of claim 1, further comprising a blunt stylet having a blunt distal tip, the blunt stylet receivable in the cannula when the sharp stylet is removed.

3. The system of claim 2, wherein the blunt stylet is receivable in the cannula before the plug is received in the cannula.

4. The system of claim 2, wherein a portion of the cannula is flexible.

5. The system of claim 1, wherein the plug is configured to securely lodge distal to the side aperture of the cannula.

6. The system of claim 5, wherein the plug is tapered externally to complement the tapered internal surface of the cannula.

7. The system of claim 5, wherein an outer dimension of the plug is less than an inner diameter of the cannula proximal to the tapered internal surface and greater than an inner diameter of the cannula at the tapered internal surface.

8. The system of claim 7, wherein the plug is substantially cylindrical.

9. The system of claim 7, wherein the plug is substantially spherical.

10. The system of claim 1, wherein a proximal end of the plug is sloped.

11. The system of claim 10, wherein the side aperture is a slot having an elongated shape, the system configured to align the sloped end of the plug with the slot in the cannula when the plug is received in the cannula and sealing the distal opening.

12. The system of claim 1, wherein the push rod has a length such that at its limit the push rod is not at the distal opening.

13. The system of claim 1, further comprising a handle assembly including a cannula handle attached to the cannula and a stylet handle attached to the sharp stylet, the cannula and stylet handles configured to interlock to secure the stylet in the cannula.

14. The system of claim 13, further comprising a connector at the cannula handle to connect to a syringe for aspirating or delivering material through the cannula, the stylet handle covering the connector when the stylet and cannula handles interlock.

15. The system of claim 13, further comprising an adjustable depth guide to move the cannula when the cannula is positioned within bone, the depth guide including a lead screw attached to the cannula handle and a threaded jacket receivable on the lead screw.

16. The system of claim 1, wherein the cannula defines plural side apertures.

17. A method of accessing bone, comprising:
inserting a cannula and a sharp stylet positioned in the cannula into bone, the cannula defining a side aperture in a side of the cannula and a distal opening at a distal tip of the cannula, the cannula including a tapered internal surface near the distal tip of the cannula, the stylet having a sharp distal tip that extends through the distal opening;

removing the sharp stylet from the cannula;

pushing a plug through the cannula and distal to the side aperture to seal the distal opening of the cannula, the plug configured to securely lodge against the tapered internal surface of the cannula, wherein pushing the plug includes pushing the plug with a push rod separate from the plug and receivable in the cannula; and accessing the bone through the side aperture of the cannula.

18. The method of claim 17, wherein accessing the bone includes aspirating bone marrow through the side aperture.

19. The method of claim 17, wherein accessing the bone includes injecting a substance into the bone through the side aperture.

20. The method of claim 17, wherein accessing the bone includes inserting an instrument through the side aperture into the bone.

21. The method of claim 17, wherein inserting the cannula and stylet into the bone comprises advancing the cannula and stylet into the bone with an adjustable depth guide.

22. The method of claim 21, further comprising withdrawing the cannula from the bone with the adjustable depth guide.

* * * * *